(12) United States Patent
Hoshino

(10) Patent No.: US 8,510,890 B2
(45) Date of Patent: Aug. 20, 2013

(54) ELECTRIC TOOTHBRUSH

(75) Inventor: Junichi Hoshino, Higashioumi (JP)

(73) Assignee: Panasonic Corporation, Osaka (JP)

( * ) Notice: Subject to any disclaimer, the term of this patent is extended or adjusted under 35 U.S.C. 154(b) by 293 days.

(21) Appl. No.: 13/071,840

(22) Filed: Mar. 25, 2011

(65) Prior Publication Data

US 2011/0232011 A1  Sep. 29, 2011

(30) Foreign Application Priority Data

Mar. 25, 2010 (JP) .................................. 2010-071134

(51) Int. Cl.
*A61C 17/34* (2006.01)

(52) U.S. Cl.
USPC ........................................... 15/22.1; 15/22.2

(58) Field of Classification Search
USPC ........................................ 15/22.1, 22.2, 22.4
See application file for complete search history.

(56) References Cited

U.S. PATENT DOCUMENTS

| | | | |
|---|---|---|---|
| 5,406,664 A | 4/1995 | Hukuba | |
| 2008/0183249 A1* | 7/2008 | Kitagawa et al. | 607/79 |
| 2009/0188057 A1 | 7/2009 | Kunita et al. | |
| 2011/0016648 A1* | 1/2011 | Kunita et al. | 15/22.1 |

FOREIGN PATENT DOCUMENTS

| | | |
|---|---|---|
| CN | 1034124 A | 7/1989 |
| CN | 1040918 A | 4/1990 |
| CN | 1187341 A | 7/1998 |
| CN | 2011-94850 Y | 2/2009 |
| EP | 1955730 A1 | 1/2008 |
| EP | 1908434 A1 | 4/2008 |
| EP | 2082704 A1 | 7/2009 |
| JP | 60-45362 | 3/1985 |
| JP | 05-003807 | 1/1993 |
| JP | 2008-183378 | 8/2008 |
| JP | 2009-125428 | 6/2009 |
| JP | 2009-125482 | 6/2009 |
| JP | 2009-172316 | 8/2009 |
| JP | 2009-219544 | 10/2009 |
| JP | 2009-233121 | 10/2009 |

OTHER PUBLICATIONS

European Search Report in corresponding EP Application No. 11159519.5, dated Oct. 29, 2012, pp. 1-6.
Official Communication of Japanese Application 2010-071134 mailed on Jul. 10, 2012.
Office Action dated Feb. 22, 2013 in a corresponding Chinese patent application.

\* cited by examiner

*Primary Examiner* — Randall Chin
(74) *Attorney, Agent, or Firm* — Wolf, Greenfield & Sacks, P.C.; Randy J. Pritzker

(57) ABSTRACT

An electric toothbrush provided with a function for oscillating a brush body by rotating a weight and a function for applying current inside a user's mouth. The electric toothbrush includes a brush body. A main body includes an attachment shaft, which is formed by a conductive member. The brush body is attached to the attachment shaft. A weight is arranged in the attachment shaft. A motor rotates the weight and oscillates the brush body through the attachment shaft. A power supply is arranged in the main body. A first electrode is connected to the power supply. The first electrode is arranged on the main body in a state exposed from a surface of the main body. A second electrode is connected to the power supply. The second electrode is arranged on the brush body in a state exposed from a surface of the main body.

6 Claims, 3 Drawing Sheets

ELECTRIC TOOTHBRUSH

CROSS-REFERENCE TO RELATED APPLICATIONS

This application is based upon and claims the benefit of priority from prior Japanese Patent Application No. 2010-071134, filed on Mar. 25, 2010, the entire contents of which are incorporated herein by reference.

BACKGROUND OF THE INVENTION

The present invention relates to an electric toothbrush including a brush body having a brush, a main body having an attachment shaft attached to the brush body, and a motor that rotates a weight to oscillate the brush body.

In the prior art, an electric toothbrush includes a brush body that is driven by a drive unit, which includes an actuator including a conversion means, such as a gear or a cam, or an actuator including a magnetic circuit structure. Japanese Laid-Open Patent Publication Nos. 2008-183378 and 2009-125428 describe examples of such an electric toothbrush provided with a current application function.

Japanese Laid-Open Patent Publication No. 2009-219544 describes an example of an electric toothbrush that rotates a weight, which is coupled to a motor, to generate oscillation.

However, an electric toothbrush that rotates a weight to generate oscillation is not provided with a current application function.

It is an object of the present invention to provide an electric toothbrush provided with a function for rotating a weight to oscillate a brush body and a function for applying current inside the mouth.

SUMMARY OF THE INVENTION

Other aspects and advantages of the present invention will become apparent from the following description, taken in conjunction with the accompanying drawings, illustrating by way of example the principles of the invention.

One aspect of the present invention is an electric toothbrush provided with a brush body including a brush. A main body includes an attachment shaft, which is formed by a conductive member and attached to the brush body. A weight is arranged in the attachment shaft. A motor rotates the weight and oscillates the brush body with the attachment shaft. A power supply is arranged in the main body. A first electrode is connected to the power supply. The first electrode is arranged on the main body in a state exposed from a surface of the main body. A second electrode is connected to the power supply. The second electrode is arranged on the brush body in a state exposed from a surface of the main body.

BRIEF DESCRIPTION OF THE DRAWINGS

The invention, together with objects and advantages thereof, may best be understood by reference to the following description of the presently preferred embodiments together with the accompanying drawings in which.

DETAILED DESCRIPTION OF THE INVENTION

First Embodiment

Figure 1:
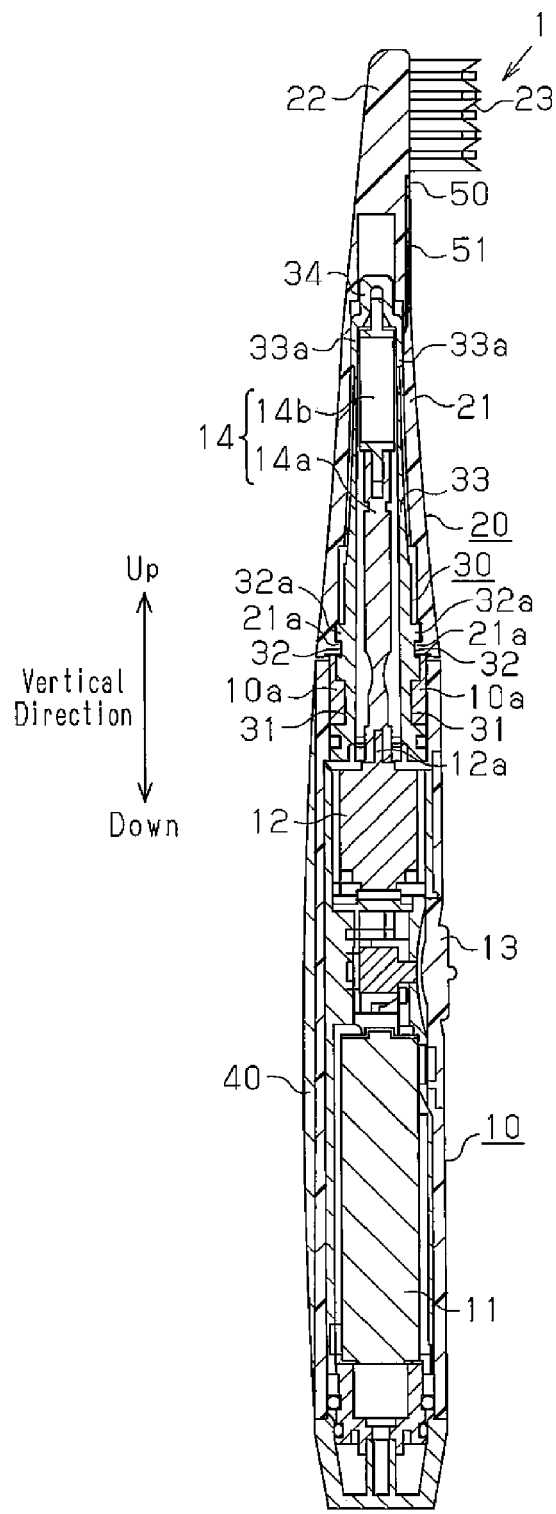
FIGS. 1(a) and 1(b) are cross-sectional views of an electric toothbrush according to a first embodiment of the present invention.
Figure 1:
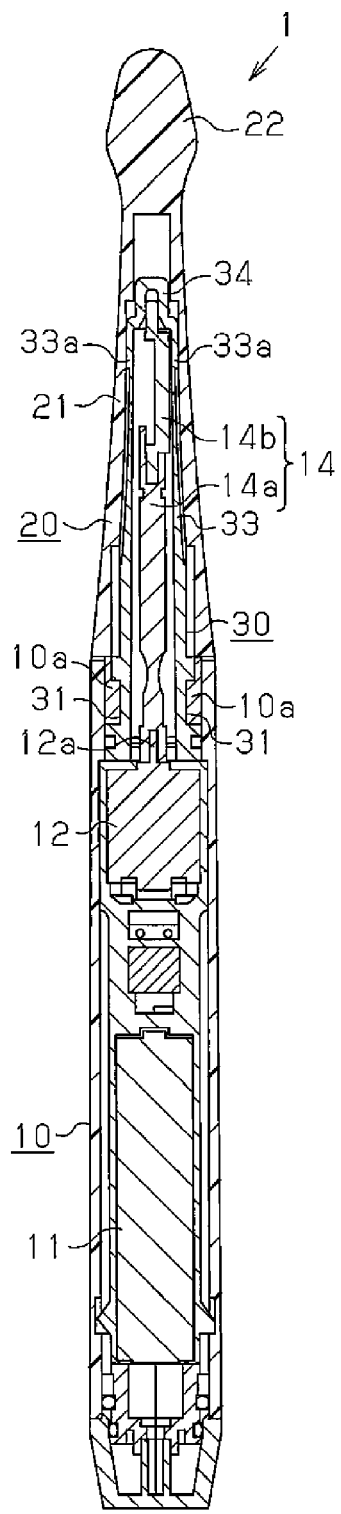
Figure 2:
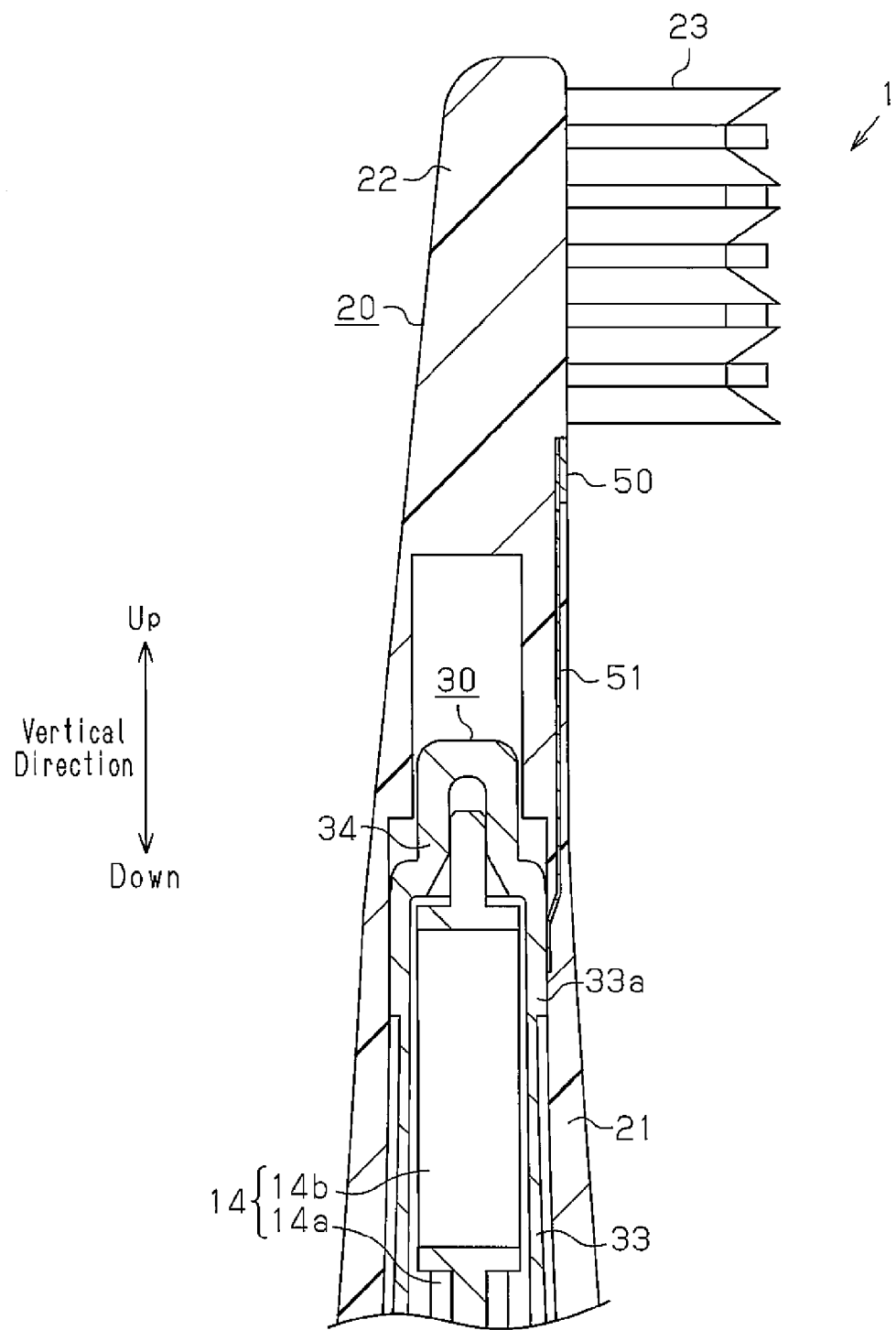
FIG. 2 is an enlarged partial cross-sectional view of the electric toothbrush shown in FIG. 1(a)

An electric toothbrush 1 according to a first embodiment of the present invention will now be discussed with reference to FIGS. 1 and 2. In the description hereafter, the longitudinal direction of the electric toothbrush 1 will be defined as the vertical direction.

As shown in FIGS. 1(a) and 1(b), the electric toothbrush 1 includes a main body 10 and a brush body 20. The main body 10 is cylindrical, has a closed bottom, and is held by a user when brushing the user's teeth. The brush body 20 is attached in a removable manner to the main body 10. The main body 10 is formed from an insulative material.

The main body 10 accommodates a power supply 11 and a motor 12. The power supply 11 is formed by a rechargeable battery that can be charged and discharged. The motor 12 is driven using the power supply 11 as a drive source.

The main body 10 includes a switch 13, which opens and closes an electric line connecting the power supply 11 and the motor 12. The motor 12 includes a rotary shaft 12a. An eccentric shaft 14 is attached to the rotary shaft 12a. The eccentric shaft 14 includes an elongated shaft body 14a and a weight 14b, which is arranged on the top end of the shaft body 14a. The center of gravity of the weight 14b deviates from the rotation axis of the rotary shaft 12a.

The main body 10 includes a cylindrical attachment shaft 30. The brush body 20 is attached to the attachment shaft 30, which is formed by a nonmetal conductive member. The nonmetal conductive member may be formed from synthetic resin containing carbon fibers. ABS resin may be used as such a synthetic resin.

The attachment shaft 30 includes an attached portion 31, a fastening portion 32, a shaft accommodation portion 33, and a shaft support portion 34. The attached portion 31 is attached to the top part of the main body 10. The fastening portion 32 fastens the bottom part of the brush body 20. The shaft accommodation portion 33 accommodates the eccentric shaft 14. The shaft support portion 34 supports a distal end of the weight 14b in a rotatable manner.

The shaft body 14a and weight 14b of the eccentric shaft 14 are inserted into the attachment shaft 30. The attached portion 31 and fastening portion 32 are defined by recesses and projections formed on the outer surface of the attachment shaft 30. The attached portion 31 is fixed to the main body 10. An oscillation absorber 10a, which absorbs the oscillation generated by the rotation of the weight 14b, is arranged between the attached portion 31 and the main body 10. The oscillation absorber 10a is formed by an elastic member. The fastening portion 32 is a recess that engages a hook 21a arranged at the bottom part of the brush body 20. More specifically, a fastening projection 32a projects outward in the radial direction above the fastening portion 32. The fastening portion 32 is a recess extending inward in the radial direction relative to the fastening projection 32a.

A notch is formed in part of the fastening projection 32a that projects out of the attachment shaft 30. To fasten the brush body 20 to the main body 10, the hook 21a is inserted into the notch, and the brush body 20 is rotated relative to the main body 10. This engages the hook 21a with the fastening projection 32a. The fastening portion 32 includes a ridge, which slightly projects outward in the radial direction and extends in the axial direction. When the brush body 20 is rotated, the hook 21a clicks as it moves over the ridge of the fastening portion 32. The user can feel the click and recognize the fastening of the brush body 20.

The shaft accommodation portion 33 is cylindrical and has an inner diameter that is generally constant in the vertical direction. The shaft body 14a and weight 14b of the eccentric shaft 14 are arranged in the shaft accommodation portion 33 slightly spaced from the inner surface of the shaft accommodation portion 33. The outer surface of the shaft accommodation portion 33 is shaped in conformance with the inner surface of the brush body 20. A rib 33a projects slightly outward in the radial direction, which is orthogonal to the vertical direction, from the top part of the shaft accommodation portion 33. The rib 33a of the shaft accommodation portion 33 contacts the inner surface of the brush body 20 when attached to the main body 10.

The rib 33a serves as a transmission portion that transmits the oscillation generated by the rotation of the weight 14b to the brush body 20. The shaft support portion 34 is coupled to the top part of the shaft accommodation portion 33. The shaft support portion 34 supports the top end of the weight 14b, which is the top end of the eccentric shaft 14.

The brush body 20 is formed from a resin material and includes a tube 21 and a head 22. The attachment shaft 30 is inserted into the tube 21. The head 22 is arranged on the top part of the tube 21 and formed from an insulative material. The head 22, which is a brush, includes bundled bristles 23 used to clean teeth.

Figure 3A:
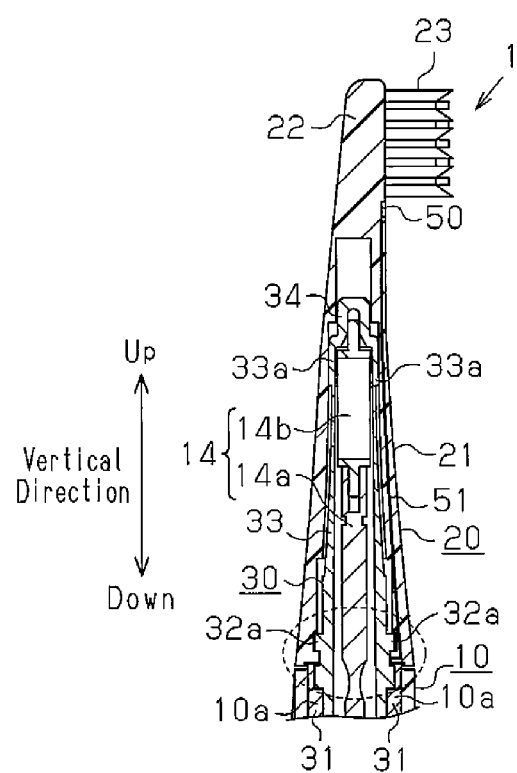
FIG. 3(a) is a cross-sectional view of an electric toothbrush according to a second embodiment of the present invention.
Figure 3B:
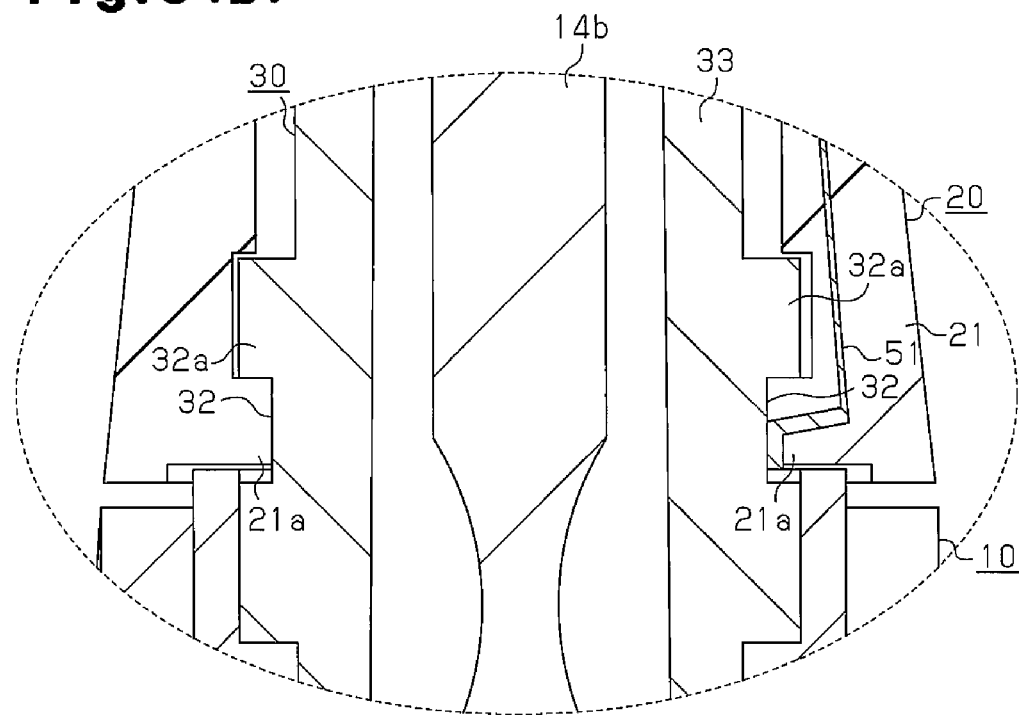
FIG. 3(b) is an enlarged partial cross-sectional view of the electric toothbrush shown in FIG. 3(a).

The hook 21a is arranged at the bottom part of the tube 21, or the bottom part of the brush body 20. The hook 21a extends inward in the radial direction from the surface of the tube 21. The hook 21a engages the fastening projection 32a. This restricts upward movement of the brush body 20 relative to the main body 10 and fastens the brush body 20 to the main body 10. The brush body 20 is fastened to the main body 10 in a state in which the hook 21a is held on the ridge arranged on the fastening portion 32. Thus, the hook 21a is in contact with the fastening portion 32, as shown in FIG. 3(b). This drawing shows a cross-section of the fastening portion 32 at a location that includes the ridge.

The tube 21 encloses the attachment shaft 30 of the main body 10. The rib 33a is in contact with the inner surface of the tube 21. As a result, the oscillation generated by the rotation of the weight 14b is transmitted by the rib 33a to the brush body 20. This oscillates the brush body 20.

The configuration for applying current to the user will now be discussed in detail.

The main body 10 includes a first electrode 40 electrically connected via a conductor (not shown) to a first terminal of the power supply 11. The first electrode 40 is exposed from the outer surface of the main body 10. The first electrode 40 serves as a finger electrode that comes into contact with the user's fingers, which hold the main body 10.

The brush body 20 includes a second electrode 50 electrically connected via a conductor 51 to a second terminal of the power supply 11. The second electrode 50 is exposed from the outer surface of the head 22 near the bundled bristles 23. The second electrode 50 serves as a mouth electrode that comes into contact with the user's mouth when the user inserts the head 22 into his or her mouth to brush the user's teeth.

The conductor 51 is embedded in the tube 21 and the head 22. The top part of the conductor 51 is connected to the second electrode 50. The bottom part of the conductor 51 is connected to the rib 33a of the attachment shaft 30.

The attachment shaft 30 is connected by another conductor (not shown) to the second terminal of the power supply 11.

Thus, the second electrode 50 is electrically connected via the conductor 51 and the attachment shaft 30 to the power supply 11.

In a state in which the brush body 20 is detached from the main body 10, the bottom part of the conductor 51, that is, the part of the conductor 51 that contacts the rib 33a of the attachment shaft 30, is inclined toward the rib 33a. When the conductor 51 contacts the rib 33a, the rib 33a forces the conductor 51 outward so that the conductor 51 comes into close contact with the rib 33a. This clamps the bottom part of the conductor 51 between the rib 33a and the brush body 20.

The switch 13 electrically connects and disconnects the attachment shaft 30 and power supply 11. More specifically, when the switch 13 is on, an electric line connecting the power supply 11 and the second electrode 50 is closed.

The operation of the electric toothbrush 1 will now be discussed.

The user uses the electric toothbrush 1 while holding the main body 10 and touching the first electrode 40. When the user turns on the switch 13, the power supply 11 supplies power to the motor 12. This produces rotation with the motor 12 and rotates the shaft body 14a and weight 14b of the eccentric shaft 14. In this state, the oscillation of the weight 14b is transmitted to the brush body 20 by the rib 33a. This oscillates the brush body 20.

Further, when the user turns on the switch 13, a conductive circuit is formed extending from the first terminal of the power supply 11 to the first electrode 40, the user's body (i.e., fingers, torso, and mouth), the second electrode 50, the conductor 51, the attachment shaft 30, and to the second terminal of the power supply 11. As a result, current flows into the user's mouth during tooth brushing. When current of about 100 µA (microamperes) flows in the mouth, a preferable massaging effect on the gum is obtained. The current that flows in the mouth can be either direct current or alternating current. Further, the current supplied is not limited to a constant current and may be a pulsed current.

The present embodiment has the advantages described below.

(1) The power supply 11 is arranged in the main body 10. Further, the first electrode 40, which is connected to the power supply 11, is arranged on the main body 10 in a state exposed from the surface of the main body 10. The second electrode 50, which is exposed from the surface of the main body 10, is arranged on the brush body 20 in a state exposed from the surface of the brush body 20. Further, the attachment shaft 30, which accommodates the weight 14b, is formed by the conductive member. Accordingly, in a state in which the first electrode 40 and second electrode 50 are connected to the power supply 11, which is arranged in the main body 10, the user holds the main body 10, from which the first electrode 40 is exposed, to perform tooth brushing. In this state, part of the brush body 20, from which the second electrode 50 is exposed, is in contact with the mouth. As a result, current flows into the mouth.

(2) The rib 33a, which serves as a transmission portion that transmits the oscillation generated by the rotation of the weight 14b to the brush body 20, is arranged on the attachment shaft 30. Further, the second electrode 50 is electrically connected to the rib 33a of the attachment shaft 30. In this manner, the rib 33a functions to transmit oscillation to the brush body 20 and also functions to electrically connect the power supply 11 and second electrode 50.

(3) The attachment shaft 30 is formed by the nonmetal conductive member. Thus, in comparison to when the attachment shaft 30 is formed by a metal conductive member, corrosion of the attachment shaft 30 is limited.

Second Embodiment

An electric toothbrush 1 according to a second embodiment of the present invention will now be discussed with reference to FIG. 3. To avoid redundancy, like or same reference numerals are given to those components that are the same as the corresponding components of the first embodiment. FIG. 3(b) is an enlarged cross-sectional view of the section encircled by a broken line in FIG. 3(a).

When the brush body 20 is fastened to the main body 10, the hook 21a and the conductor 51 are in contact with the fastening portion 32. This electrically connects the attachment shaft 30 and the conductor 51. That is, the bottom part of the conductor 51 is connected to the fastening portion 32 of the attachment shaft 30. The bottom part of the conductor 51, that is, the part that contacts the fastening portion 32 of the attachment shaft 30 is inclined toward the fastening portion 32 when the brush body 20 is detached from the main body 10. Thus, when the conductor 51 is in contact with the fastening portion 32, the fastening portion 32 forces the conductor 51 outward. As a result, the conductor 51 comes into close contact with the fastening portion 32. This clamps the bottom part of the conductor 51 between the rib 33a and the brush body 20.

In addition to advantages (1) and (3) of the first embodiment, the second embodiment has the advantage described below.

(4) The fastening portion 32, which fastens the brush body 20 to the attachment shaft 30, is arranged on the attachment shaft 30. This electrically connects the second electrode 50 to the fastening portion 32 of the attachment shaft 30. Thus, the fastening portion 32 functions to fasten the brush body 20 to the attachment shaft 30 and also functions to electrically connect the power supply 11 and the second electrode 50.

It should be apparent to those skilled in the art that the present invention may be embodied in many other specific forms without departing from the spirit or scope of the invention. Particularly, it should be understood that the present invention may be embodied in the following forms.

The power supply 11 may be formed by a primary battery, which cannot be recharged. Further, a commercial power supply outside the electric toothbrush 1 may be used as a drive source for the motor 12.

The electric connection of the attachment shaft 30 and power supply 11 does not have to cooperate with the electric connection of the motor 12 and power supply 11. For example, the electric toothbrush 1 may include a switch that is separate from the switch 13, and the switch may open and close the electric line connecting the power supply 11 and the second electrode 50.

The attachment shaft 30 may be formed by a metal conductive member.

The present examples and embodiments are to be considered as illustrative and not restrictive, and the invention is not to be limited to the details given herein, but may be modified within the scope and equivalence of the appended claims.

What is claimed is:

1. An electric toothbrush comprising:
a brush body including a brush;
a main body including an attachment shaft, which is formed by a conductive member and attached to the brush body;
a weight arranged in the attachment shaft;
a motor that rotates the weight and oscillates the brush body with the attachment shaft;
a power supply arranged in the main body;
a first electrode connected to the power supply, wherein the first electrode is arranged on the main body in a state exposed from a surface of the main body; and
a second electrode connected to the power supply, wherein the second electrode is arranged on the brush body in a state exposed from a surface of the main body.

2. The electric toothbrush according to claim 1, wherein
the attachment shaft includes a transmission portion that contacts the brush body to transmit oscillation, which is generated when the weight rotates, to the brush body; and
the second electrode is electrically connected to the transmission portion.

3. The electric toothbrush according to claim 2, wherein the second electrode includes an end portion clamped between an inner surface of the brush and a surface of the transmission portion.

4. The electric toothbrush according to claim 1, wherein
the attachment shaft includes a fastening portion that fastens the brush body to the attachment shaft; and
the second electrode is electrically connected to the fastening portion.

5. The electric toothbrush according to claim 4, wherein the second electrode includes an end portion clamped between an inner surface of the brush and a surface of the transmission portion.

6. The electric toothbrush according to claim 1, wherein the conductive member forming the attachment shaft is a non-metal.

* * * * *